(12) United States Patent
Nakanishi

(10) Patent No.: US 9,852,526 B2
(45) Date of Patent: Dec. 26, 2017

(54) METHOD AND APPARATUS OF RESAMPLING AND AVERAGING TO OBTAIN TILTED THICK-SLICE COMPUTED TOMOGRAPHY IMAGES

(71) Applicant: TOSHIBA MEDICAL SYSTEMS CORPORATION, Otawara-shi (JP)

(72) Inventor: Satoru Nakanishi, Arlington Heights, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/683,999

(22) Filed: Apr. 10, 2015

(65) Prior Publication Data

US 2016/0300367 A1    Oct. 13, 2016

(51) Int. Cl.
| | | |
|---|---|---|
| *G06K 9/00* | (2006.01) | |
| *G06T 11/00* | (2006.01) | |
| *A61B 6/03* | (2006.01) | |
| *A61B 6/02* | (2006.01) | |
| *A61B 6/04* | (2006.01) | |
| *A61B 6/00* | (2006.01) | |

(52) U.S. Cl.
CPC ............ *G06T 11/005* (2013.01); *A61B 6/032* (2013.01); *A61B 6/5223* (2013.01); *A61B 6/027* (2013.01); *A61B 6/0407* (2013.01); *A61B 6/5205* (2013.01); *G06T 2211/421* (2013.01); *G06T 2211/424* (2013.01)

(58) Field of Classification Search
None
See application file for complete search history.

(56) References Cited

U.S. PATENT DOCUMENTS

| | | | |
|---|---|---|---|
| 5,454,371 A | 10/1995 | Fenster et al. | |
| 6,061,420 A | 5/2000 | Strong et al. | |
| 6,243,438 B1 * | 6/2001 | Nahaliel | A61B 6/032 378/19 |
| 6,256,366 B1 * | 7/2001 | Lai | A61B 6/032 378/17 |
| 8,045,770 B2 * | 10/2011 | Reeves | G06T 7/0012 382/128 |
| 9,697,638 B2 * | 7/2017 | Shinohara | G06T 15/005 |

(Continued)

*Primary Examiner* — Nancy Bitar
(74) *Attorney, Agent, or Firm* — Oblon, McClelland, Maier & Neustadt, L.L.P.

(57) ABSTRACT

An apparatus and method for obtaining a thick-slice image from tilted thin-slice computed-tomography (CT) projection data. Tilted CT projection data is obtained for a series of projection planes, wherein the projection planes are parallel for all scans, and the translation direction between CT scans is not orthogonal to the projection planes (i.e., the projection planes are tilted relative to the translation direction between CT scans). Thin-slice images are reconstructed from the respective CT scans, and then grouped into thick-slice groupings. An offset results among the thin-slice images within a thick-slice grouping due to the tilt of the projection planes. This offset is compensated by interpolating and resampling the thin-slice images onto non-offset pixel grids. The interpolated and resampled thin-slice images are then averaged pixel-by-pixel to obtain thick-slice images having the same tilt angle as the thin-slice images.

20 Claims, 8 Drawing Sheets

(56) References Cited

U.S. PATENT DOCUMENTS

| | | | | |
|---|---|---|---|---|
| 2001/0028697 | A1* | 10/2001 | Nahaliel | A61B 6/032 378/19 |
| 2002/0190984 | A1* | 12/2002 | Seiler | G06T 15/005 345/424 |
| 2003/0097055 | A1* | 5/2003 | Yanof | A61B 6/032 600/407 |
| 2003/0123603 | A1* | 7/2003 | Suzuki | A61B 6/032 378/4 |
| 2004/0125103 | A1* | 7/2004 | Kaufman | G06T 15/005 345/419 |
| 2005/0113681 | A1* | 5/2005 | DeFreitas | A61B 6/502 600/426 |
| 2007/0160276 | A1* | 7/2007 | Chen | G06K 9/32 382/128 |
| 2011/0069808 | A1* | 3/2011 | DeFreitas | A61B 6/502 378/5 |
| 2013/0272494 | A1* | 10/2013 | DeFreitas | A61B 6/502 378/37 |
| 2014/0294138 | A1* | 10/2014 | Jerebko | A61B 6/025 378/4 |
| 2015/0228092 | A1* | 8/2015 | Claus | G06T 11/003 382/131 |

* cited by examiner

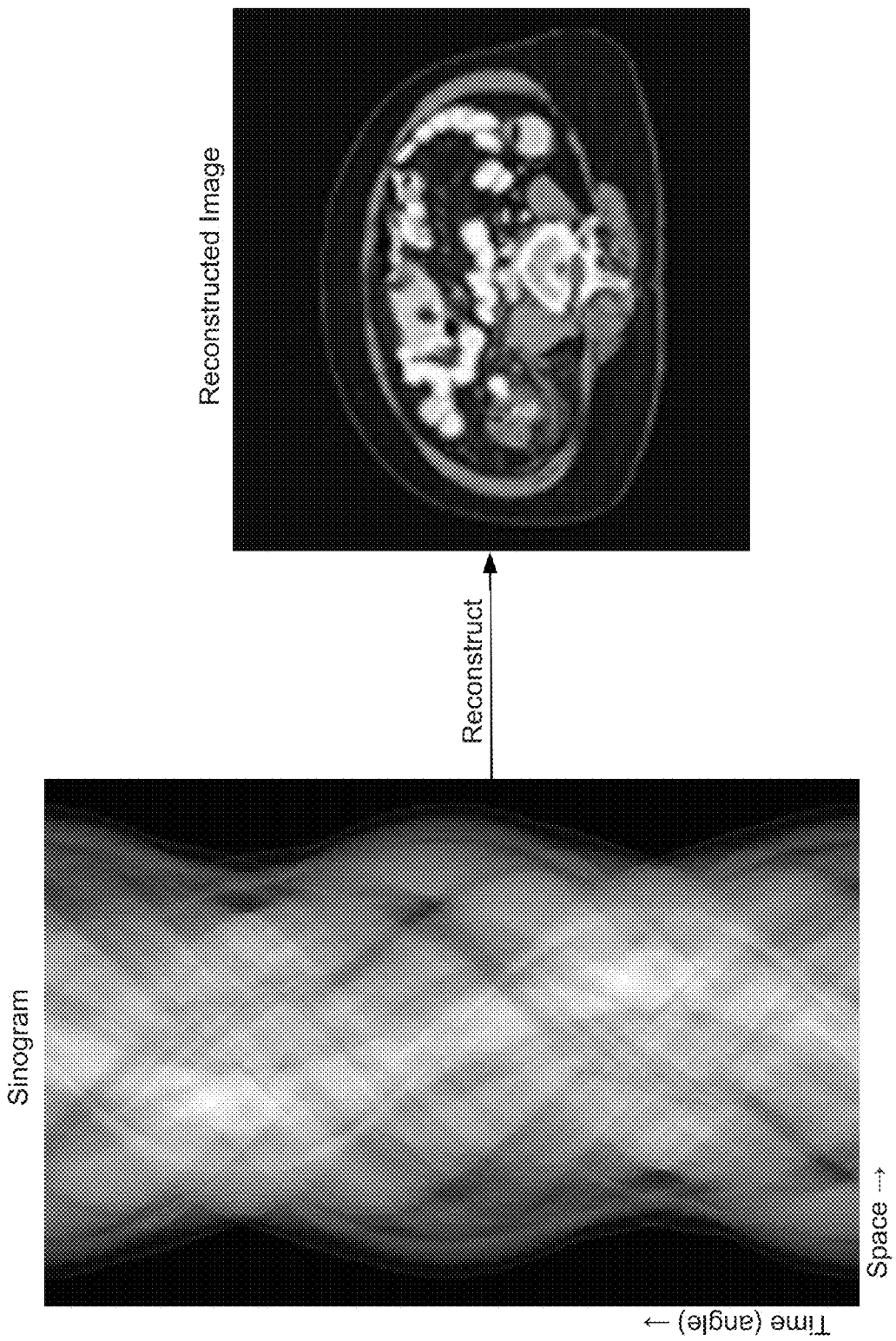

Figure 3
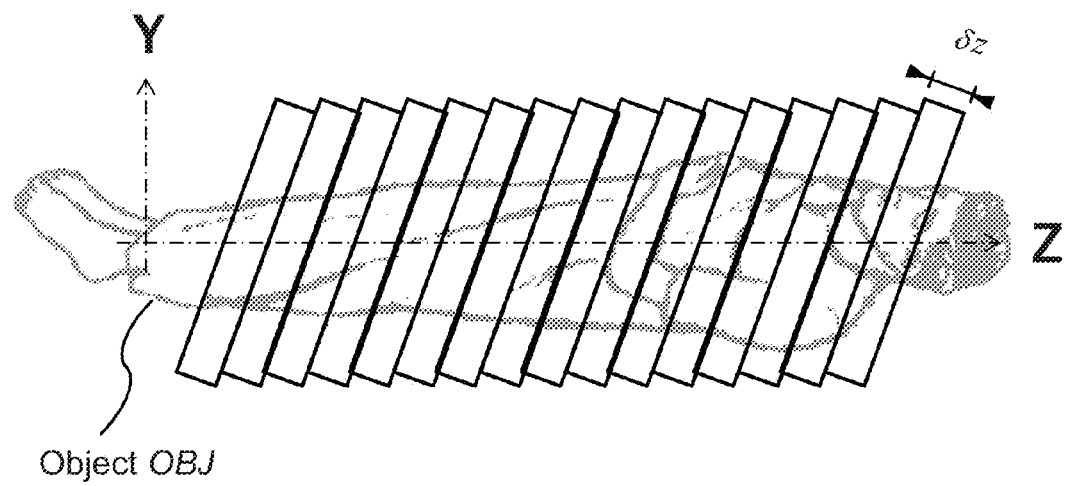
Object OBJ
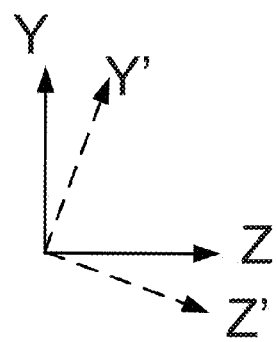

Figure 4C $$I_j$$

| $P_{1,1}^{(j)}$ | $P_{1,2}^{(j)}$ | $P_{1,3}^{(j)}$ | $\cdots$ | $P_{1,n}^{(j)}$ |
|---|---|---|---|---|
| $P_{2,1}^{(j)}$ | $P_{2,2}^{(j)}$ | $P_{2,3}^{(j)}$ | $\cdots$ | $P_{2,n}^{(j)}$ |
| $P_{3,1}^{(j)}$ | $P_{2,2}^{(j)}$ | $P_{2,3}^{(j)}$ | $\cdots$ | $P_{3,n}^{(j)}$ |
| $\vdots$ | $\vdots$ | $\vdots$ | $\ddots$ | $\vdots$ |
| $P_{m,1}^{(j)}$ | $P_{m,2}^{(j)}$ | $P_{m,3}^{(j)}$ | $\cdots$ | $P_{m,n}^{(j)}$ |

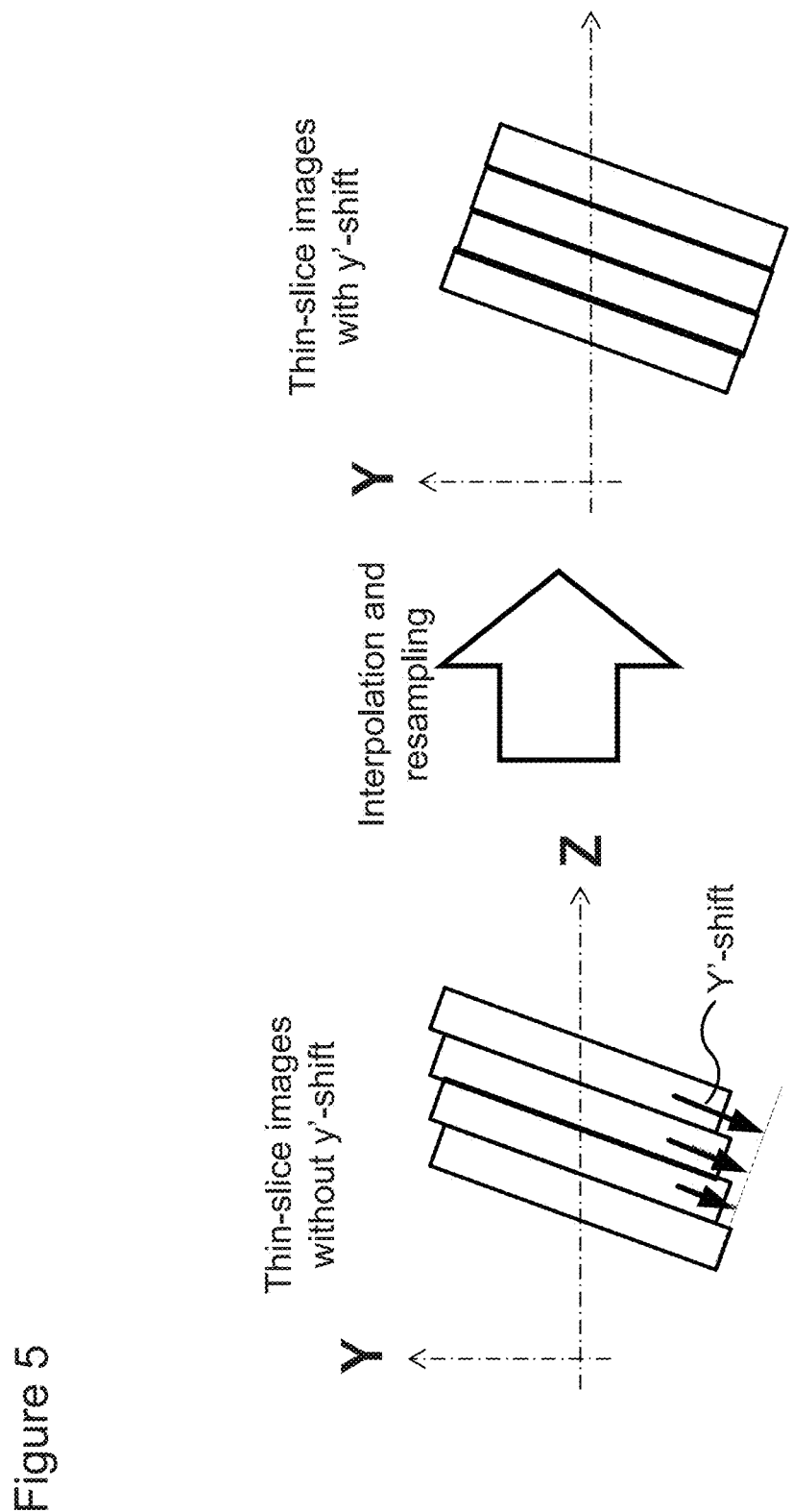

METHOD AND APPARATUS OF RESAMPLING AND AVERAGING TO OBTAIN TILTED THICK-SLICE COMPUTED TOMOGRAPHY IMAGES

BACKGROUND

Field

Embodiments described herein relate generally to a method of reconstructing computed tomography (CT) images by averaging nearest-neighbor CT images, and more specifically to averaging nearest-neighbor tilted CT images in order to reconstruct tilted CT images having a thickness greater than the slice thickness corresponding to the projection data.

Description of the Related Art

Computed tomography (CT) systems and methods are widely used, particularly for medical imaging and diagnosis. CT systems generally create images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a planar region defining a cross-sectional slice of the body. At least one detector (and generally many more than one detector) on the opposite side of the body receives radiation transmitted through the body substantially in the plane of the slice. The attenuation of the radiation that has passed through the body is measured by processing electrical signals received from the detector.

FIG. 1A shows a CT sinogram, which is a plot of attenuation through the body as a function of "space" along a detector array (horizontal) and "time/angle" of a scan of measurements performed at a series of projection angles (vertical). The space dimension refers to the position along a one-dimensional array of X-ray detectors. The time/angle dimension refers to the projection angle of X-rays changing as a function of time, such that as time progresses the projection angle increments and projection measurements are performed at a linear succession of projection angles. The attenuation resulting from a particular volume will trace out a sine wave around the vertical axis—volumes farther from the axis of rotation having sine waves with larger amplitudes, the phase of a sine wave determining the volume's angular position around the rotation axis. Performing an inverse Radon transform or equivalent image reconstruction method reconstructs an image from the projection data in the sinogram—the reconstructed image corresponding to a cross-sectional slice of the body, as shown in FIG. 1A.

The process of X-ray projection measurements of two-dimensional slices through an object onto a one-dimensional measurement plane can be represented mathematically as a Radon transformation $$g(X,z)=R[f(x,y,z)],$$

where $g(X,z)$ is the projection data as a function of position X along a detector array for a slice of thickness dz normal to the z-direction, $f(x,y,z)$ is the attenuation of the object as a function of position, and $R[\cdot]$ is the Radon transform in the x-y plane. Having measured projection data at multiple angles, the image reconstruction problem can be expressed by calculating the inverse Radon transformation of the projection data $$f(x,y,z)=R^{-1}[g(X,z,\theta)],$$

where $R^{-1}[\cdot]$ is the inverse Radon transform and $\theta$ is the projection angle at which the projection data was acquired. In practice, there are many methods for reconstructing an image $f(x,y,z)$ from the projection data $g(X,z,\theta)$.

Often the image reconstruction problem will be formulated as a matrix equation $$Af=g,$$

where g represents the projection measurements of the X-rays transmitted through an object space including the object OBJ, A is the system matrix describing the discretized line integrals (i.e., the Radon transforms) of the X-rays through the object space, and f is the image of object OBJ (i.e., the quantity to be solved for by solving the system matrix equation). Image reconstruction can be performed by taking the matrix inverse or pseudo-inverse of the matrix A. However, this rarely is the most efficient method for reconstructing an image. The more conventional approach is called filtered back projection (FBP), which consistent with the name, entails filtering the projection data and then back projecting the filtered projection data onto the image space, as expressed by $$f(x,y,z)=BP[g(X,z,\theta)*F_{Ramp}(X)].$$

where $F_{Ramp}(X)$ is a ramp filter (the name "ramp filter" arises from its shape in the spatial-frequency domain), the symbol * denotes convolution, and $BP[\cdot]$ is the back projection function.

Other methods of image reconstruction include: iterative reconstruction methods (e.g., the algebraic reconstruction technique (ART) method and the total variation minimization regularization methods), Fourier-transform-based methods (e.g., direct Fourier method), and statistical methods (e.g., maximum-likelihood expectation-maximization algorithm based methods).

While it is known how to reconstruct CT images from projection data corresponding to a given projection plane using, e.g., the iterative or filtered-back-projection methods discussed above, in some applications it is desirable to combine projection data from several adjacent thin-slice CT scans to generate a single thick-slice CT image. When the translation direction between CT scans is orthogonal to the projection planes, reconstructing a thick-slice image from thin-slice projection data can be realized by the straightforward process of averaging the projection data into thick slices and then reconstructing an image from the resulting thick-slice projection data. However, when the projection planes of the CT scans are tilted with respect to the translation direction, an offset due to the tilt can create complications in reconstructing a thick-slice image from the tilted thin-slice projection data.

BRIEF DESCRIPTION OF THE DRAWINGS

A more complete understanding of this disclosure is provided by reference to the following detailed description when considered in connection with the accompanying drawings, wherein:

FIG. 1A shows an example of sinogram data and the reconstructed tomographic image resulting from performing computed tomography (CT) reconstruction on the sinogram data;

FIG. 3 shows an example of the volumes corresponding to tilted thin-slice images;

FIG. 4C shows one implementation of a grid of pixels and corresponding nomenclature for both the thick-slice images and the thin-slice images;

FIG. 5 shows one implementation of shifting the thin-slice image in a y-direction to compensate for the pixel offset resulting from the tilt of the CT apparatus.

DETAILED DESCRIPTION

In one embodiment, there is provided an image-processing apparatus, comprising: (1) an interface configured to receive projection data representing an irradiance of radiation detected at a plurality of detectors, the projection data corresponding to a plurality of scan slices measured at a non-zero tilt angle; and (2) processing circuitry configured to (i) reconstruct a plurality of thin-slice images, wherein each of the plurality of thin-slice images corresponds to a respective scan slice of the plurality of scan slices, (ii) group the plurality of thin-slice images into thick-slice groupings corresponding to subsets of nearest-neighbor thin-slice images, (iii) shift the thin-slice images within a thick-slice grouping to compensate for an offset resulting from the tilt angle, and (iv) average, pixel-by-pixel, each thick-slice grouping to obtain a thick-slice image.

In another embodiment, there is provided a computed-tomography (CT) apparatus, comprising: (1) a radiation source radiating radiation into an object space; (2) a plurality of detector elements configured to detect the radiation transmitted from the radiation source and through the object space, wherein the plurality of detector elements configured to generate projection data; (3) a rotation mount configured to rotate the radiation source around the object space, wherein the radiation source is fixedly connected to the rotation mount; and (4) processing circuitry configured to: (i) receive the projection data representing the irradiance of the radiation detected at a plurality of detectors, wherein the projection data corresponds to a plurality of scan slices measured at a non-zero tilt angle, (ii) reconstruct a plurality of thin-slice images, wherein each of the plurality of thin-slice images corresponds to a respective scan slice of the plurality of scan slices, (iii) group the plurality of thin-slice images into thick-slice groupings corresponding to subsets of nearest-neighbor thin-slice images, (iv) shift the thin-slice images within a thick-slice grouping to compensate for an offset resulting from the tilt angle, and (v) average, pixel-by-pixel, each thick-slice grouping to obtain a thick-slice image.

Figure 1B:
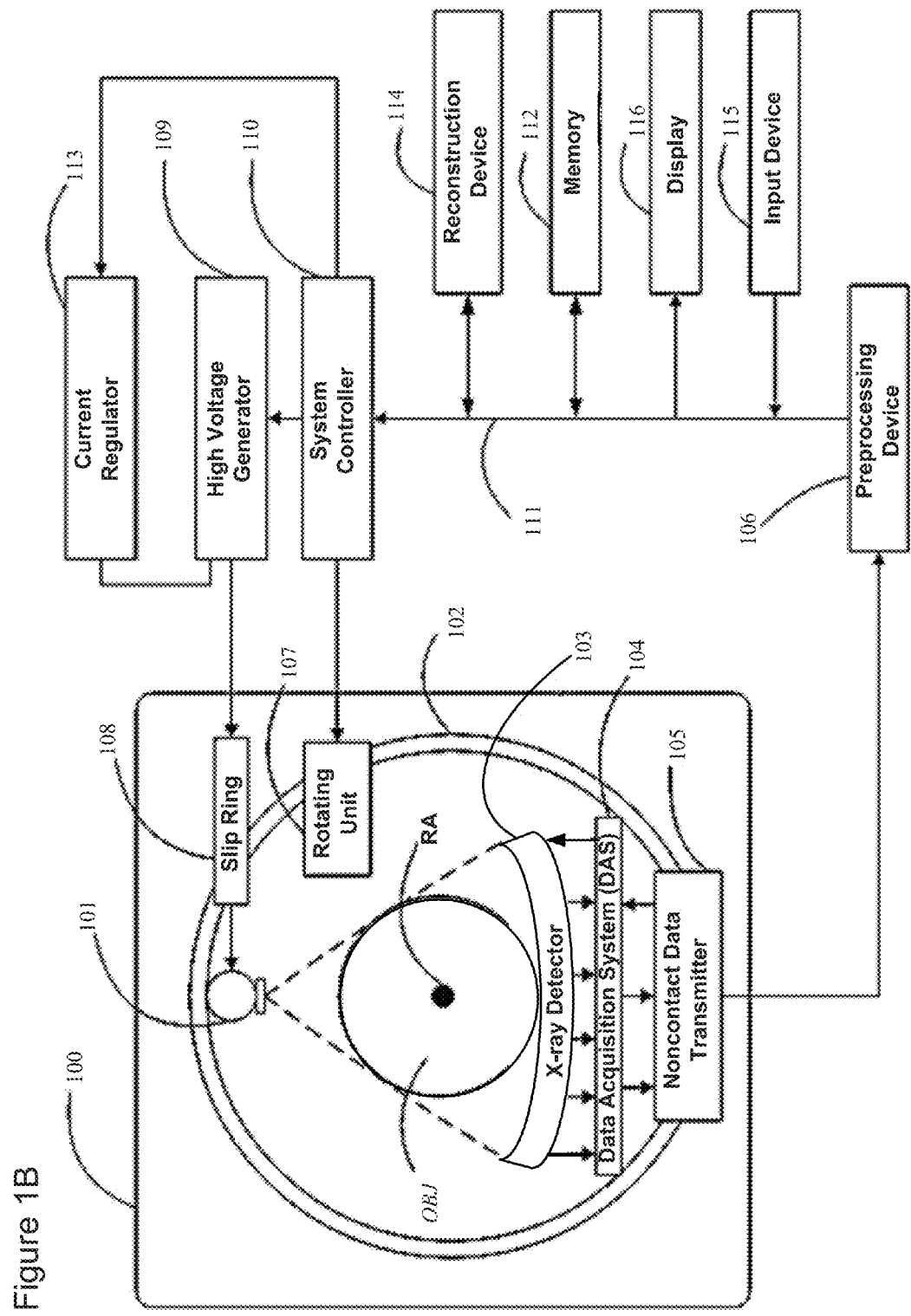
FIG. 1B shows a schematic drawing of one implementation of a CT apparatus having a source and detectors for measuring CT projection data.

Referring now to the drawings, wherein like reference numerals designate identical or corresponding parts throughout the several views, FIG. 1BB illustrates an implementation of the radiography gantry included in a CT apparatus or scanner. As shown in FIG. 1B, a radiography gantry 100 is illustrated from a side view and further includes an X-ray tube 101, an annular frame 102, and a multi-row or two-dimensional-array-type X-ray detector 103. The X-ray tube 101 and X-ray detector 103 are diametrically mounted across an object OBJ on the annular frame 102, which is rotatably supported around a rotation axis RA. A rotating unit 107 rotates the annular frame 102 at a high speed, such as 0.4 sec/rotation, while the object OBJ is being moved longitudinally along the axis RA into or out of the illustrated page.

Note that X-ray computed tomography apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 109 that generates a tube voltage applied to the X-ray tube 101 through a slip ring 108 so that the X-ray tube 101 generates X-rays. The X-rays are emitted towards the object OBJ, whose cross sectional area is represented by a circle. The X-ray detector 103 is located at an opposite side from the X-ray tube 101 across the object OBJ for detecting the emitted X-rays that have transmitted through the object OBJ. The X-ray detector 103 further includes individual detector elements or units.

The CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal. The X-ray detector 103 and the DAS 104 are configured to handle a predetermined total number of projections per rotation (TPPR). Examples of TPPRs include, but are not limited to 800 TPPR, 900 TPPR, 900-1800 TPPR, and 900-3600 TPPR.

The above-described data is sent to a preprocessing device 106, which is housed in a console outside the radiography gantry 100 through a non-contact data transmitter 105. The preprocessing device 106 performs certain corrections, such as sensitivity correction on the raw data. A memory 112 stores the resultant data, which is also called projection data at a stage immediately before reconstruction processing. The memory 112 is connected to a system controller 110 through a data/control bus 111, together with a reconstruction device 114, input device 115, and display 116. The system controller 110 controls a current regulator 113 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 101 and the X-ray detector 103 are diametrically mounted on the annular frame 102 and are rotated around the object OBJ as the annular frame 102 is rotated about the rotation axis RA. In the fourth-generation geometry system, the detectors are fixedly placed around the patient and an X-ray tube rotates around the patient. In an alternative embodiment, the radiography gantry 100 has multiple detectors arranged on the annular frame 102, which is supported by a C-arm and a stand.

The memory 112 can store the measurement value representative of the irradiance of the X-rays at the X-ray detector unit 103. Further, the memory 112 can store a dedicated program that executes, e.g., the CT image reconstruction method 600 discussed herein.

The reconstruction device 114 can execute the CT image reconstruction method 600 discussed herein. Further, reconstruction device 114 can execute pre-reconstruction processing image processing such as volume rendering processing and image difference processing as needed. The pre-reconstruction processing of the projection data performed by the preprocessing device 106 can include correcting for detector calibrations, detector nonlinearities, polar effects, noise balancing, and material decomposition. Post-reconstruction processing performed by the reconstruction device 114 can include filtering and smoothing the image, volume rendering processing, and image difference processing as needed. The image reconstruction process can be performed using filtered back-projection (FBP), iterative image reconstruction methods, or stochastic image reconstruction methods. The reconstruction device 114 can use the memory 112 to store, e.g., projection data, reconstructed images, calibration data and parameters, and computer programs.

The reconstruction device 114 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 112 can be non-volatile, such as ROM, EPROM, EEPROM or FLASH memory. The memory 112 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 114 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 116. The display 116 can be an LCD display, CRT display, plasma display, OLED, LED or any other display known in the art.

The memory 112 can be a hard disk drive, CD-ROM drive, DVD drive, FLASH drive, RAM, ROM or any other electronic storage known in the art.

Figure 2:
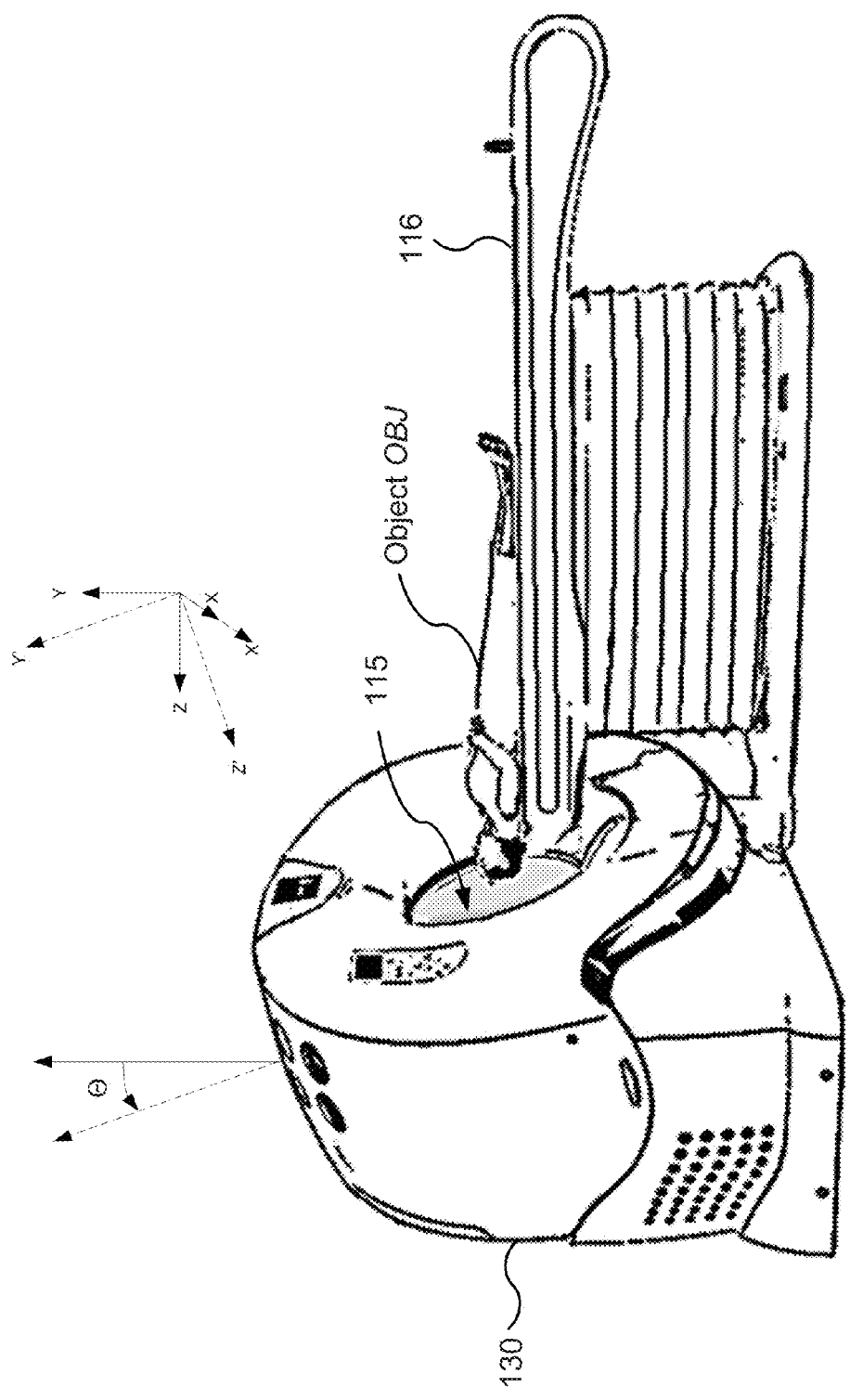
FIG. 2 shows a drawing of one implementation of a CT apparatus wherein the normal vector to the projection plane is tilted at angle Θ relative to the translation direction of the imaged object between CT scans.

FIG. 2 shows a drawing of a computed tomography apparatus that has been tilted in the Y-Z plane to obtain projection data of tilted slices through the object OBJ. The projection data are measured for a series of scans corresponding to different values of z (i.e., the position of the bed 116 relative to the intersection of the rotation axis of the CT apparatus with the projection plane). In FIG. 2, the projection plane X'-Y' is not orthogonal to the translation direction of table 116 (i.e., the Z-direction). Therefore the projection data and the resulting slice images will also not be orthogonal to the translation direction. The projection data and the reconstructed images are said to be tilted at the tilt angle Θ. The Euclidean coordinates (x,y,z) corresponding to the un-tilted reference frame can be related to the coordinates (x',y',z') of the tilted reference frame using the transformation $$\begin{bmatrix} X' \\ Y' \\ Z' \end{bmatrix} = \begin{bmatrix} 1 & 0 & 0 \\ 0 & \cos\Theta & \sin\Theta \\ 0 & -\sin\Theta & \cos\Theta \end{bmatrix} \begin{bmatrix} X \\ Y \\ Z \end{bmatrix}.$$

FIG. 3 shows a drawing of the tilted slices through the object. These slices can be referred to as micro-slices or as thin slices, which have a thickness of δz. For each thin slice the CT apparatus acquires projection data within the projection plane at a series of projection angles. The projection data for each thin slice can be reconstructed into a two-dimensional image of the attenuation within the thin-slice volume.

Figure 4A:
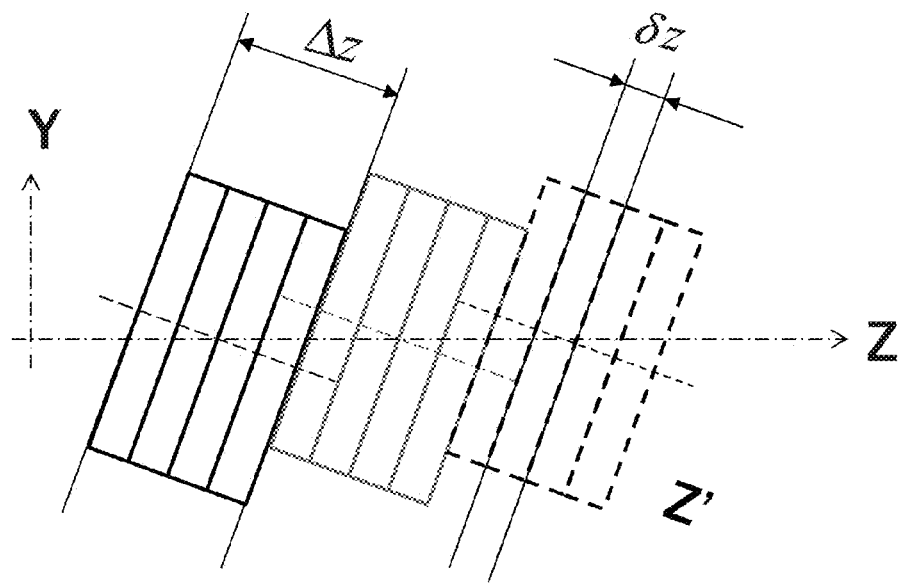
FIG. 4A shows one implementation of grouping thin-slice images into thick-slice groupings, wherein the relative y-offset among thin-slice images has been compensated for in preparation for averaging the groupings of thin-slice images to create a thick slice image.
Figure 4B:
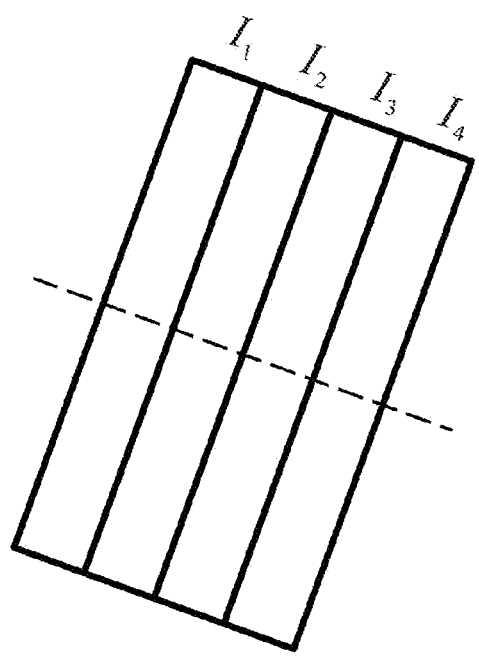
FIG. 4B shows an example of a thick-slice grouping, wherein each thin-slice image is labeled.

In some applications and implementations of CT imaging, thick-slice images are desired over thin-slice images. FIG. 4A shows an example of thick-slice images having a thickness of Δz. The thick-slice images can be chosen to have a thickness Δz that is an integer multiple of the thin-slice image thickness δz. For example, in FIG. 4 the thick-slice images are four times as thick as the thin-slice images, but Δz can be any integer multiple of δz. FIG. 4B shows that the thin-slice images can respectively be labeled using subscripts such as $I_1$, $I_2$, $I_3$, and $I_4$, wherein a continuous group of thin-slice images is referred to as a thick-slice grouping when there is intent to average these thin-slice images to create thick-slice images.

As shown in FIG. 4C, each thin image $I_j$ has pixels designated by $P_{n,m}^{(j)}$, which are labeled according to their position within the pixel grid, wherein n indicates the row, m indicates the column, and j indicates the image subscript, for example. The thick image can be obtained by averaging over the thin images to obtain $$P_{n,m}^{(thick)} = \frac{1}{N_{Thin}} \sum_{j=1}^{N_{Thin}} P_{n,m}^{(j)},$$

wherein $P_{n,m}^{(thick)}$ are the pixels of the thick image and $N_{Thin}$ is the number of thin slices to be averaged. The thin-slice images within a thick-slice grouping are defined as "nearest neighbors" in the sense that they represent a continuous block of adjacent thin-slice images.

Before averaging the thin images to obtain thick images, the offset of the thin image grids can be overcome by interpolating and resampling the thin-slice images onto a new grid that is shifted in the y-direction. FIG. 5 shows that without correcting for the tilt offset, the thin-slice images each have an image center corresponding to the same y value (e.g., y=0). However, the relevant coordinate system for averaging the thin images is the transformed coordinates (x',y',z') because the transformed coordinates correspond to the projection plane. In the transformed coordinates, the thin-slice images each exhibit a y'-offset relative to their neighboring images. FIG. 5 shows one example of correcting for the tilt induced y'-offset by shifting each thin-slice image within a thick-slice grouping such that the center point of the image remains within the same respective projection plane, but is shifted relative to the first thin-slice image by the amount $$y'_{shift}=(1-j)\tan\Theta\delta z.$$

For example, a y'-shifted grid can be determined for each thin-slice image, wherein the shifted grid positions are derived from the un-shifted grid positions to be $$x'^{(shift)}_{n,m,j}=x'_{n,m,j} \quad \text{and} \quad y'^{(shift)}_{n,m,j}=y'_{n,m,j}+(1-j)\tan\Theta\delta z.$$

After determining the y'-shifted grid for each thin-slice image, the corresponding reconstructed image can be interpolated from the original grid onto the y'-shifted grid. This process of interpolating the thin-slice images onto shifted pixel grids is one example of how the tilt offset can be compensated for by interpolating and resampling the thin-slice images.

Any known interpolation function can be used, including, e.g., a nearest neighbor interpolation method, a linear interpolation method, a quadratic interpolation method, a cubic interpolation method, a spline interpolation method, a cubic Hermite interpolation method, a Lagrange polynomial interpolation method, a Newton-Cotes interpolation method, and a Lanczos resampling interpolation method. Some of the y'-shifted grid points might lie outside the un-shifted pixel grid of the thin-slice image. Thus the interpolation method can also include extrapolating to obtain these border image pixels that are outside the original pixel grid. The extrapolation method can be any known method, including polynomial extrapolation methods similar to the interpolation methods discussed above and including the method of setting these out-of-original-grid pixels to a value of zero attenuation. Setting these border image values to zero attenuation can be effective because the image region is generally chosen to be sufficiently large so that no significant image structure is located at the boundaries.

Figure 6:
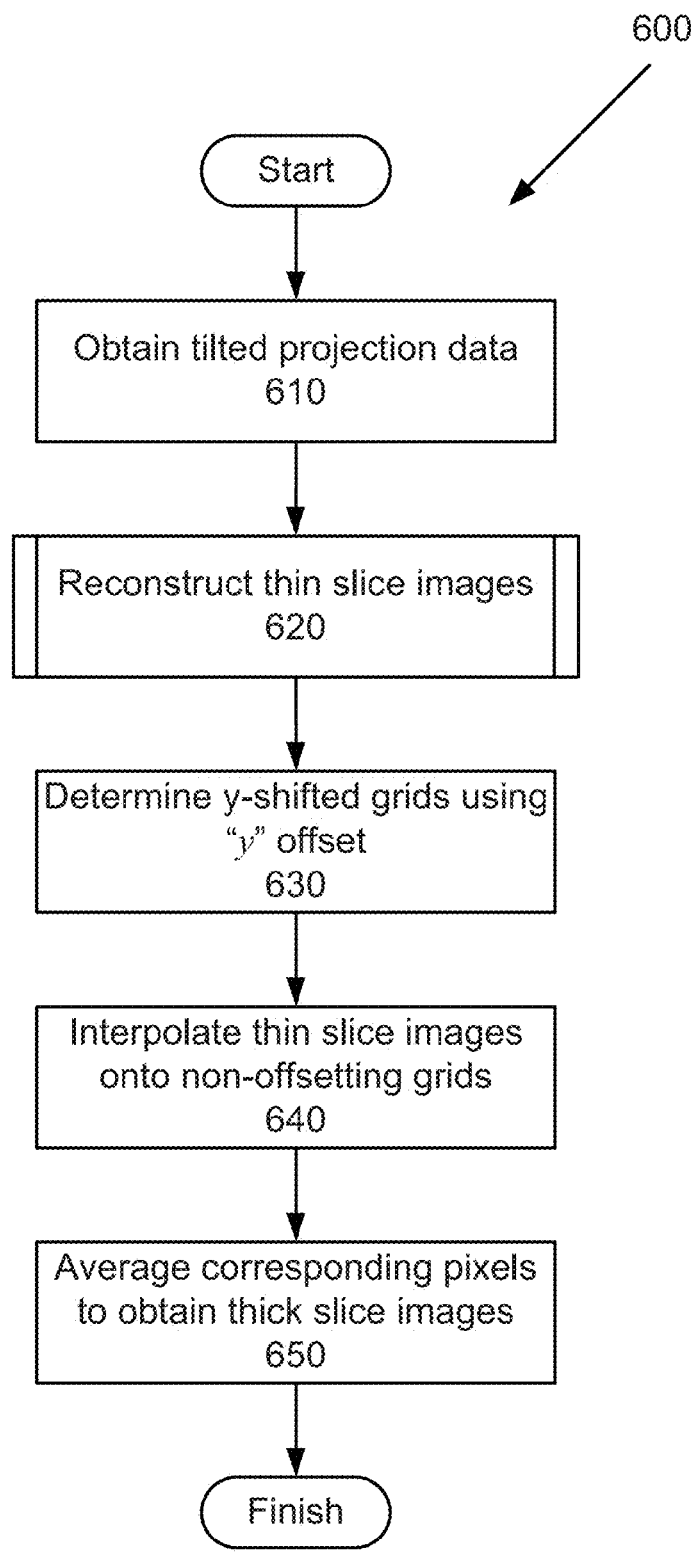
FIG. 6 shows one implementation of a method for compensating for the pixel offset among a grouping of thin-slice images in order to average the thin-slice images to obtain thick-slice images.

FIG. 6 shows a method 600 of obtaining tilted thick-slice images from tilted thin-slice projection data. As discussed above, the first step 610 in obtaining tilted thick-slice images using method 600 is obtaining thin-slice projection data using a tilted CT apparatus, e.g., as shown in FIG. 2.

Next, at step 620 of method 600, the thin-slice images are reconstructed from the thin-slice projection data. Each thin-slice image can be reconstructed from the corresponding projection data using any known CT reconstruction method. For example, the CT reconstruction method can be performed using filtered back-projection, iterative image reconstruction methods, or stochastic image reconstruction methods. Further, the CT reconstruction method can be any back-projection method (e.g., filtered back-projection), any iterative reconstruction method (e.g., the algebraic reconstruction technique (ART) method and the total variation minimization regularization methods), any Fourier-transform-based method (e.g., the direct Fourier method), or a statistical method (e.g., the maximum-likelihood expectation-maximization algorithm based methods). Furthermore, if a full scan is not performed, then a short-scan CT reconstruction method can be used, such as the Dreike-Boyd parallel rebinning algorithms, complementary rebinning algorithms, applying suitable weighting function such as the Parker weights to the sinogram, the Katsevich's method, and the Feldkamp method. One of ordinary skill will recognize that many methods of CT reconstruction are possible depending on the type of detectors, source, scan, object, and desired image.

Next, at step 630 of method 600, y'-shifted grids are determined for each thin-slice image. While the relative y-shift among the thin-slice images is important, the absolute q-shift is somewhat arbitrary for all of the thin-slice images within a thick-slice grouping (i.e., so long as the relative shift among the thin-slice images compensates for the offset resulting from the tilt, the exact value of the shift is less significant). Thus, the absolute y-shift can be tailored to the particular requirements of a given CT apparatus and measurement. For example, in one implementation, the y-shift of the pixel grid is given by $$y'_{n,m,j}=y'_{n,m,j}+(1-j)\tan\Theta\delta z.$$

In another implementation, the y-shift of the pixel grid is given by $$y'_{n,m,j}=y'_{n,m,j}+((N_{Thin}-1)/2-j)\tan\Theta\delta z.$$

In some implementations, a different absolute y-shift among different thick slices is used.

Next, at step 640 of method 600, the thin-slice images are interpolated onto the y'-shifted pixel grids. The interpolated thin-slice images then correspond to the shifted thin-slice images in FIG. 4A, wherein thick-slice groupings of thin-slice images are aligned to a common transformed coordinate system [X',Y',Z'] and there is no relative offset in the y'-direction among the shifted thin-slice images.

Next, at step 650 of method 600, the groupings of shifted thin-slice images are averaged pixel-by-pixel to obtain the thick-slice image. In one implementation, the pixel-by-pixel averaging is performed according to $$P^{(thick)}_{n,m} = \frac{1}{N_{Thin}} \sum_{j=1}^{N_{Thin}} P^{(j)}_{n,m}.$$

In another implementation, the thin-slice pixels are averaged using a weighted average:

$$P^{(thick)}_{n,m} = \left(\sum w^{j}_{m,n}\right)^{-1} \sum_{j=1}^{N_{Thin}} w^{j}_{m,n} \times P^{(j)}_{n,m},$$

wherein $w^{j}_{m,n}$ the weighted value for the pixel $P^{(j)}_{n,m}$.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. A computed-tomography (CT) apparatus, comprising:
processing circuitry configured to
receive projection data representing an irradiance of radiation detected at a plurality of detectors, the projection data corresponding to a plurality of parallel scan slices measured at a non-zero tilt angle, reconstruct a plurality of thin-slice images, wherein each thin-slice image of the plurality of thin-slice images corresponds to a respective scan slice of the plurality of parallel scan slices, and the thin-slice image of the plurality of thin-slice images lies in a plane corresponding to the non-zero tilt angle, group the plurality of thin-slice images into thick-slice groupings corresponding to subsets of nearest-neighbor thin-slice images, and shift the thin-slice images within a thick-slice grouping based on a distance calculated using the tilt angle.

2. The CT apparatus according to claim 1, wherein the processing circuitry is further configured to shift the thin-slice images by performing a shift in a tilt-offset direction to resample the nearest-neighbor thin-slice images, wherein the tilt-offset direction lies in both a projection plane and in a tilt plane tilted by the tilt angle.

3. The CT apparatus according to claim 2, wherein the shift in the tilt-offset direction is performed by interpolating the plurality of nearest-neighbor thin-slice images to resample the thin-slice images onto an offset-compensated grid.

4. The CT apparatus according to claim 2, wherein the shift in the tilt-offset direction for a predetermined thin-slice image is given by a product of a tangent of the tilt angle and a shortest distance between the projection plane of the predetermined thin-slice image and a predetermined reference plane that is parallel to the projection plane of the predetermined thin-slice image.

5. The CT apparatus according to claim 3, wherein the processing circuitry is further configured to interpolate the thin-slice images using one of a linear interpolation method, a quadratic interpolation method, a cubic interpolation method, a spline interpolation method, a cubic Hermite interpolation method, a Lagrange polynomial interpolation method, a Newton-Cotes interpolation method, and a Lanczos resampling interpolation method.

6. The CT apparatus according to claim 1, wherein the processing circuitry is further configured to reconstruct the plurality of thin-slice images using an iterative reconstruction method.

7. The CT apparatus according to claim 1, wherein the processing circuitry is further configured to reconstruct the plurality of thin-slice images using a filtered-back-projection method.

8. The CT apparatus according to claim 1, further comprising:
a radiation source radiating the radiation into an object space;
the plurality of detectors configured to detect the radiation transmitted from the radiation source and through the object space, wherein the plurality of detectors are configured to generate the projection data; and
a rotation mount configured to rotate the radiation source around the object space, wherein the radiation source is fixedly connected to the rotation mount.

9. A method, comprising:
obtaining projection data representing an irradiance of radiation detected at a plurality of detectors, the projection data corresponding to a plurality of parallel scan slices measured at a non-zero tilt angle;
reconstructing a plurality of thin-slice images, wherein each thin-slice image of the plurality of thin-slice images corresponds to a respective scan slice of the plurality of parallel scan slices, and the thin-slice image of the plurality of thin-slice images lies in a plane corresponding to the non-zero tilt angle;
grouping the plurality of thin-slice images into thick-slice groupings corresponding to subsets of nearest-neighbor thin-slice images; and
shifting the thin-slice images within a thick-slice grouping based on a distance calculated using the tilt angle.

10. The method according to claim 9, wherein the step of shifting the thin-slice images comprises performing a shift in a tilt-offset direction to resample the nearest-neighbor thin-slice images, wherein the tilt-offset direction lies in both a projection plane and in a tilt plane tilted by the tilt angle.

11. The method according to claim 10, wherein the step of performing the shift in the tilt-offset direction comprises interpolating the plurality of nearest-neighbor thin-slice images to resample the thin-slice images onto an offset-compensated grid.

12. The method according to claim 10, wherein the shift in the tilt-offset direction for a predetermined thin-slice image is given by a product of a tangent of the tilt angle and a shortest distance between the projection plane of the predetermined thin-slice image and a predetermined reference plane that is parallel to the projection plane of the predetermined thin-slice image.

13. The method according to claim 11, wherein the step of interpolating the plurality of nearest-neighbor thin-slice images comprises performing one of a linear interpolation method, a quadratic interpolation method, a cubic interpolation method, a spline interpolation method, a cubic Hermite interpolation method, a Lagrange polynomial interpolation method, a Newton-Cotes interpolation method, and a Lanczos resampling interpolation method.

14. The method according to claim 9, wherein the step of reconstructing the plurality of thin-slice images comprises performing an iterative reconstruction method.

15. The method according to claim 9, wherein the step of reconstructing the plurality of thin-slice images comprises performing a filtered-back-projection method.

16. An image-processing apparatus, comprising:
processing circuitry configured to
receive projection data representing an irradiance of radiation detected at a plurality of detectors, the projection data corresponding to a plurality of parallel scan slices measured at a non-zero tilt angle,
reconstruct a plurality of thin-slice images, wherein each thin-slice image of the plurality of thin-slice images corresponds to a respective scan slice of the plurality of parallel scan slices, and the thin-slice image of the plurality of thin-slice images lies in a plane corresponding to the non-zero tilt angle
group the plurality of thin-slice images into thick-slice groupings corresponding to subsets of nearest-neighbor thin-slice images, and
shift the thin-slice images within a thick-slice grouping based on a distance calculated using the tilt angle.

17. A non-transitory computer-readable medium storing executable instructions, wherein the instructions, when executed by processing circuitry, cause the processing circuitry to perform the method according to claim 9.

18. The CT apparatus according to claim 1, wherein the processing circuitry is further configured to average, pixel-by-pixel, each thick-slice grouping to obtain a thick-slice image.

19. The method according to claim 9, further comprising averaging, pixel-by-pixel, each thick-slice grouping to obtain a thick-slice image.

20. The image-processing apparatus according to claim 16, wherein the processing circuitry is further configured to average, pixel-by-pixel, each thick-slice grouping to obtain a thick-slice image.

* * * * *